(12) United States Patent
Kuhns et al.

(10) Patent No.: US 8,353,847 B2
(45) Date of Patent: Jan. 15, 2013

(54) METHOD FOR ENDOLUMINALLY OR LAPAROSCOPICALLY EXCISING A TISSUE SAMPLE FROM AREAS IN A PATIENT'S BODY, TRACTION MEANS AND KIT

(75) Inventors: Jesse J. Kuhns, Cincinnati, OH (US); Alessandro Pastorelli, Rome (IT); Michele D'Arcangelo, Rome (IT); Federico Bilotti, Aprillia (IT); Brian James Thompson, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 621 days.

(21) Appl. No.: 12/279,544

(22) PCT Filed: Nov. 27, 2006

(86) PCT No.: PCT/EP2006/011347
§ 371 (c)(1),
(2), (4) Date: Nov. 6, 2008

(87) PCT Pub. No.: WO2007/101463
PCT Pub. Date: Sep. 13, 2007

(65) Prior Publication Data
US 2009/0221934 A1    Sep. 3, 2009

(30) Foreign Application Priority Data
Mar. 7, 2006  (IT) .............................. MI2006A0411

(51) Int. Cl.
*A61B 10/00* (2006.01)
*A61B 17/10* (2006.01)
*A61B 17/32* (2006.01)
*A61B 17/04* (2006.01)

(52) U.S. Cl. ...... 600/564; 606/139; 606/170; 227/180.1
(58) Field of Classification Search .... 227/175.1–182.1; 600/120–125, 562–568; 606/138–150, 167, 606/170
See application file for complete search history.

(56) References Cited

U.S. PATENT DOCUMENTS
5,122,147 A * 6/1992 Sewell, Jr. ..................... 606/110
(Continued)

FOREIGN PATENT DOCUMENTS
WO   WO 93/09721 A   5/1993
(Continued)

OTHER PUBLICATIONS
International Search Report Application No. PCT/EP2006/011347, dated Mar. 30, 2007.

*Primary Examiner* — Max Hindenburg
*Assistant Examiner* — John Pani
(74) *Attorney, Agent, or Firm* — Dean L. Garner

(57) ABSTRACT

Traction means (14) for excising a tissue sample comprising a distal portion (14a), comprising at least one clip (20) suitable for being fixed to at least one portion (12) of tissue to be excised and a proximal portion (14b) suitable for being subjected to traction. Said at least one clip (20) is suitable for being connected to a distal end (22a) of a suture (22) to pull the tissue to be excised, said suture (22) extending between said distal end (22a) and a proximal end corresponding to the proximal portion of said traction means (14). Moreover, said at least one clip (20) is connected to a ring (24) formed at a distal end (24a) of said suture (22) to pull the tissue to be excised.

45 Claims, 12 Drawing Sheets

U.S. PATENT DOCUMENTS

| | | | |
|---|---|---|---|
| 5,290,299 A * | 3/1994 | Fain et al. | 606/142 |
| 5,304,183 A | 4/1994 | Gourlay et al. | |
| 5,336,231 A | 8/1994 | Adair | |
| 5,454,820 A * | 10/1995 | Kammerer et al. | 606/148 |
| 6,352,503 B1 * | 3/2002 | Matsui et al. | 600/104 |
| 6,629,630 B2 * | 10/2003 | Adams | 227/180.1 |
| 6,632,227 B2 * | 10/2003 | Adams | 606/110 |
| 2002/0065523 A1 | 5/2002 | McAlister et al. | |
| 2002/0165589 A1 * | 11/2002 | Imran et al. | 607/40 |
| 2003/0069472 A1 * | 4/2003 | Butler | 600/121 |
| 2003/0233142 A1 | 12/2003 | Morales et al. | |
| 2005/0171470 A1 * | 8/2005 | Kucklick et al. | 604/96.01 |

FOREIGN PATENT DOCUMENTS

WO     WO 98/48701 A     11/1998

* cited by examiner

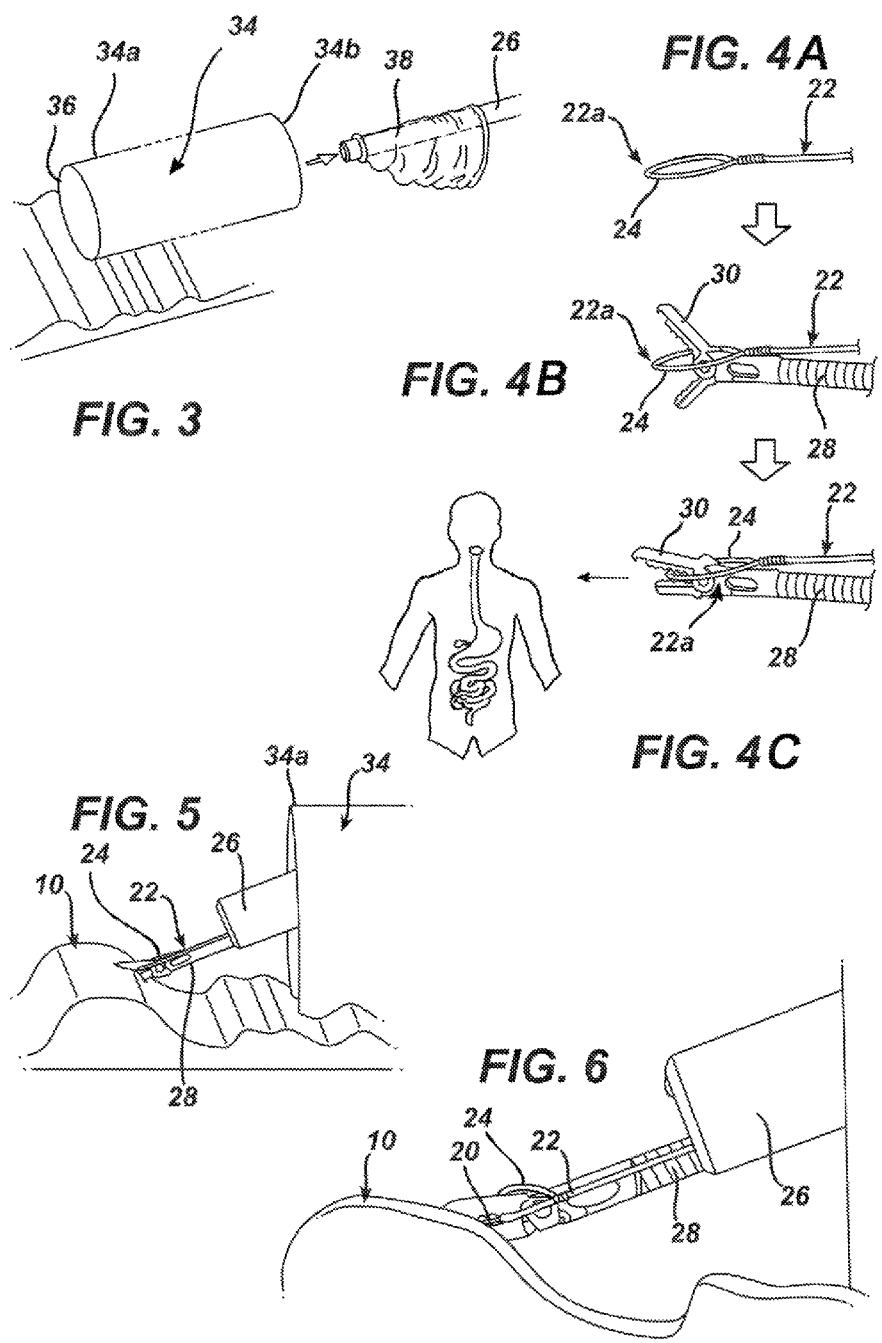

METHOD FOR ENDOLUMINALLY OR LAPAROSCOPICALLY EXCISING A TISSUE SAMPLE FROM AREAS IN A PATIENT'S BODY, TRACTION MEANS AND KIT

The present invention concerns a method for endoluminally or laparoscopically excising a tissue sample from areas in a patient's body.

In accordance with a further aspect, the present invention also concerns traction means for excising a tissue sample and a kit for endoluminally or laparoscopically excising a tissue sample from areas in a patient's body.

In particular, the present invention concerns a method suitable for covering low and high gastrointestinal portions, laparoscopic approaches and more advanced transgastric, transvaginal or transanal/rectal approaches.

There is a great need for a method and instruments suitable for endoluminally or laparoscopically excising a tissue sample from areas in a patient's body so as to allow the safe and effective removal of a tissue sample, for example a lesion. In particular, there is a need for a method and instruments for excising a determined and precise amount of tissue allowing better control of the visual field during each step of the method.

Even if surgical methods for excising tissue samples have been applied, they do not allow endoluminal or laparoscopic approaches. The disadvantages of conventional surgical methods are well known; for example, they are very invasive, the patient needs to be anaesthetised and the post-operation recovery time is long.

It is an object of the present invention to foresee a method for endoluminally or laparoscopically excising a tissue sample, having a determined amount and volume, from areas in a patient's body.

Another object of the present invention is to foresee a method for endoluminally or laparoscopically excising a tissue sample suitable for being made both for large and small amounts of tissue.

A further object of the present invention is to foresee a method for endoluminally or laparoscopically excising a tissue sample allowing better control of the visual field during each step of the method.

Yet another object of the present invention is to foresee a method for endoluminally or laparoscopically excising a tissue sample carried out along the entire length of the colon up to the caecum.

Yet another object of the present invention is to foresee a safe method for endoluminally or laparoscopically excising a tissue sample avoiding perforations.

According to a further aspect, an object of the present invention is to provide instruments like traction means or a kit suitable for being used in a laparoscopic or endoluminal method as indicated previously. A further object of the present invention is to provide instruments as indicated previously, to allow the safe and effective traction and removal of a tissue sample.

In brief, the present invention concerns a method for endoluminally or laparoscopically excising a tissue sample from areas in a patient's body comprising the steps of cutting and stapling an appropriate amount of tissue pulled through a window of a surgical stapling device by means of traction means.

Advantageously, the traction means comprise at least one clip connected to a suture for putting into traction the tissue through said window. The suture can be pulled directly from outside the patient or can be pulled by grasping means.

Each step of the present method can be carried out by means of or under the control of a visualization device (endoscope or laparoscope) for displaying the field and/or for arranging means suitable for carrying out the steps of the present method.

Advantageously, the step of introducing said at least one clip into the patient's body and fixing it to the tissue that must be excised is carried out by means of grasping means that grasp the tissue before fixing said clip to it.

In accordance with an embodiment of the invention, a sheath is introduced into the patient's body as a first step. The sheath defines a work channel for receiving the devices that carry out the method, particularly the traction means and the surgical stapling device. Moreover, the sheath is particularly advantageous to avoid perforations of the walls, in particular of the walls of the colon when the present method is carried out to endoluminally excise a tissue sample of the colon. Preferably, the sheath is introduced by means of and under the control of a visualization device fixed to the sheath. Advantageously, the surgical stapling device is guided along the work channel of the sheath, sliding on a track of the sheath.

In accordance with another embodiment of the present invention, the sheath defines a first work channel and a second work channel. The first work channel is suitable for receiving said traction means and said surgical stapling device, the second work channel is suitable for receiving a visualization device. The suture of the traction means can be fixed to the inside of the first work channel during the introduction of the sheath or else it can be introduced through the first work channel by means of positioning grasping means or of a visualization device.

Generally, a proximal portion of the traction means is inserted through the window of the surgical stapling device by which the surgical stapling device is guided by the traction means.

Advantageously, in particular when a large amount of tissue must be excised, the step of fixing said traction means to at least one portion of tissue that must be excised comprises the step of fixing a plurality of clips of said traction means to the tissue that must be excised.

Each clip of said plurality of clips is connected to a suture to put into traction the tissue through said window. The clips can be fixed along the border of the portion of tissue that must be excised. Otherwise one or more clips can be fixed directly to the portion of tissue that must be excised.

In accordance with an embodiment of the present invention, the tissue that must be excised is highlighted through a mark or tattoo and the amount of tissue pulled through the window of the surgical stapling device is monitored by checking the position of the marks or tattoos.

The aforementioned purposes, the characteristics and advantages of the invention shall become clear from the following description with reference to the attached drawings, in which:

FIG. 3 is a schematic perspective view of a further step of the method according to the present invention;

FIGS. 4A to 4C are schematic perspective views of a sequence of phases of a step of a method according to the present invention;

FIG. 5 is a schematic perspective view of a further step of a method according to the present invention;

FIG. 6 is a schematic side view of a further step of a method according to the present invention;

FIGS. 1-13 illustrate a first embodiment of a method for endoluminally or laparoscopically excising a tissue sample from areas in a patient's body according to the present invention.

Figure 1:
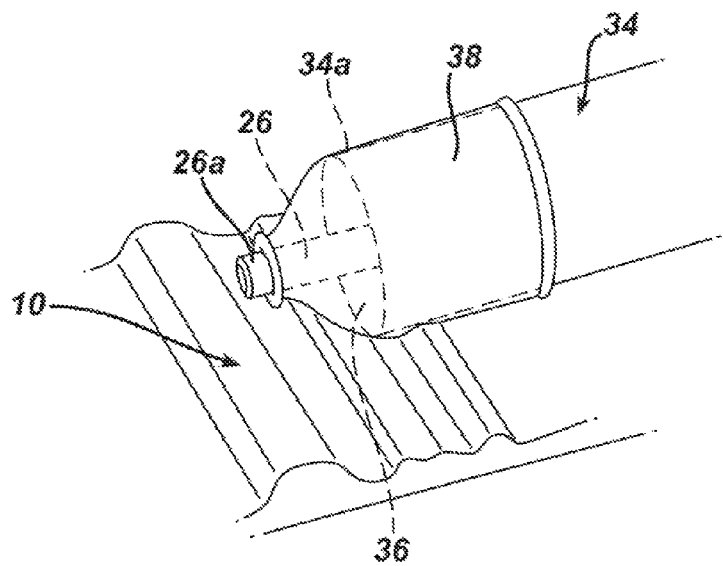
FIG. 1 is a schematic perspective view of a step of a preferred embodiment of the method for endoluminally or laparoscopically excising a tissue sample from areas of a patient's body according to the present invention.

The following description refers both to laparoscopic and endoluminal approaches in which some steps are carried out by means of and under the control of a visualization device (generic term to indicate a visualization device suitable for the chosen approach). In particular, in the case of the endoluminal approach, the steps are carried out through an endoscope.

A portion of tissue comprising the portion of tissue to be excised 12 has been generically indicated with 10. This portion can correspond to a lesion or other abnormalities that need to be examined.

Generally, the method according to the present invention comprises the steps of:

providing traction means 14 having a distal portion 14a, suitable for being fixed to at least one portion 12 of the tissue to be excised, and a proximal portion, introducing said distal portion 14a of said traction means 14 into the patient's body and positioning said distal portion 14a of said traction means 14 close to the tissue to be excised 12, by which at least one portion of said traction means 14 that extends from said distal portion 14a is positioned in the patient's body, fixing said distal portion 14a of said traction means 14 to at least one portion of tissue to be excised 12, providing a surgical stapling device 16 having a distal end 16a with a window 18 for receiving the tissue to be excised 12 and comprising cutting and stapling means that act through said window 18, introducing said surgical stapling device 16 into the patient's body and positioning said distal end 16a of the surgical stapling device close to the tissue to be excised 12, exerting traction on said traction means 14 by which an amount of tissue is pulled through said window 18, cutting and stapling said tissue by actuating said cutting and stapling means of said surgical stapling device 16 through said window 18.

Finally, all of the devices are withdrawn and the sample fixed to the traction means is removed from the patient's body.

The example of FIGS. 1-13 shows a method in which said distal portion 14a of said traction means 14 comprises at least one clip 20 by which the step of fixing said distal portion 14a of said traction means 14 to at least one portion of tissue to be excised 12 is carried out by fixing said at least one clip of said traction means to the tissue to be excised. Moreover, the clip 20 is connected to a distal end 22a of a suture 22 of said traction means to pull the tissue through said window 18. Indeed, said suture 22 extends between said distal end 22a and a proximal end corresponding to the proximal portion of said traction means 14.

Preferably, the clip 20 of said traction means 14 is connected to a ring 24 formed at a distal end 24a of said suture 22 to pull the tissue through said window 18.

As shall be described in greater detail, the step of exerting traction on said traction means 14 can comprise the step of pulling said proximal end of the suture 22 from outside the patient.

Figure 22:
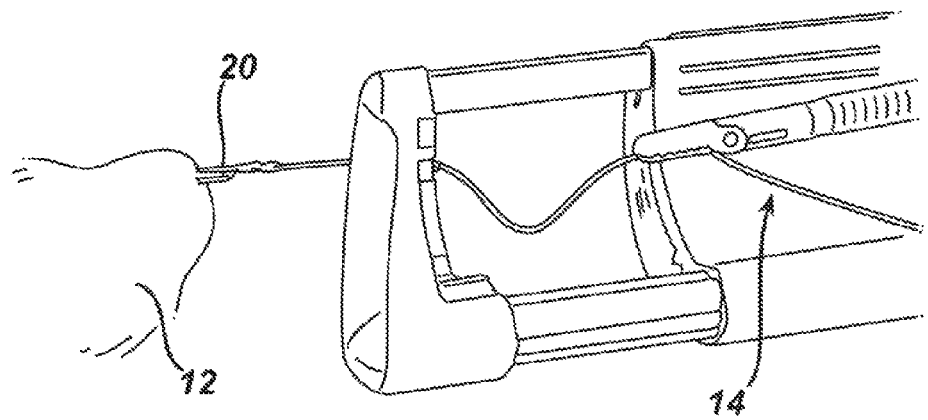
Figure 23:
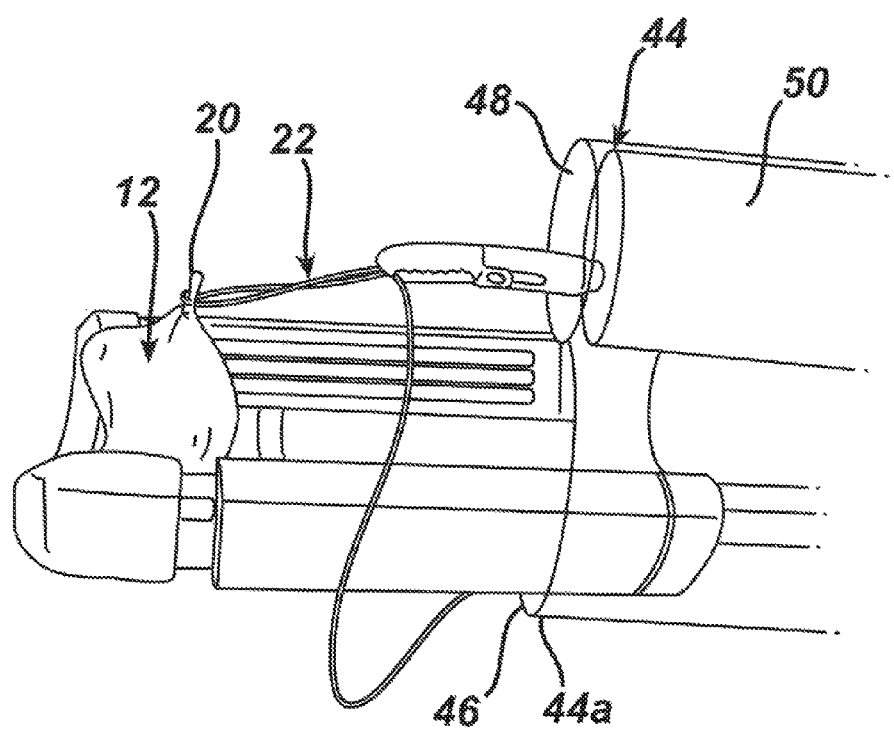

According to a different embodiment of the invention, not shown in FIGS. 1-13, the step of exerting traction on said traction means can comprise the step of pulling said proximal end of the suture 22 by means of grasping means. An example of this step is shown in FIGS. 22 and 23 with reference to a different embodiment, but it can also be carried out in the method shown in FIGS. 1-13.

Preferably, the step of exerting traction on said traction means is carried out under the control of a visualization device 26. In particular, during the step of exerting a traction on said traction means 14, a portion of said suture 22 extends through said visualization device 26 (FIG. 13) by which the proximal end of the suture 22 comes out from the proximal end of the visualization device 26 and the distal end 22a of the suture 22 comes out from an end of the visualization device 26.

According to a different embodiment of the invention, not shown in FIGS. 1-13, during the step of exerting traction on said traction means, a portion of said suture 22 extends along an outer surface of a visualization device 26.

As for example shown in FIG. 6, if the traction means comprise at least one clip 20, it is connected to the suture 22 whilst the clip is formed in the tissue and fixed to it. Preferably, the step of introducing said at least one clip into the patient's body and fixing it in the tissue to be excised is carried out by means of grasping means 28 that grasp the tissue before fixing the clip to it, as shown in FIGS. 5 and 6. For example, these grasping means can be used to introduce and fix the clip with the suture to the tissue to be excised and, after having introduced the surgical stapling device, to pull the proximal end of the suture 22 before cutting and stapling said tissue.

In the case in which said grasping means 28 are used, the ring 24 of the suture 22 is positioned in jaws 30 of said grasping means 28 (FIG. 4). The jaws are closed around said ring 24 before introducing the grasping means 28 into the patient's body and before fixing said at least one clip to the tissue to be excised (FIGS. 5 and 6).

Preferably, as shown in FIGS. 4-6, the step of introducing said traction means 14 into the patient's body is carried out under the control of a visualization device. In particular, the step of introducing said traction means 14 into the patient's body comprises the step of inserting said grasping means 28 through the visualization device 26 outside of the patient's body, and then introducing said visualization device and said grasping means into the patient's body to fix said traction means to the tissue to be excised. In this case, the suture 22 can be inserted into a channel 32 of said visualization device 26, before introducing said visualization device 26 and said grasping means 28 into the patient's body. According to a different embodiment that is not illustrated, the suture 22 can extend along the outside of the visualization device 26 before introducing said visualization device 26 and said grasping means 28 into the patient's body.

Figure 7:
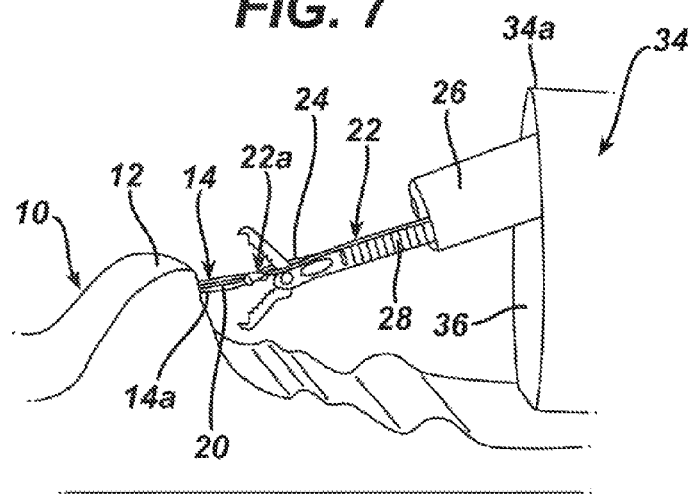
FIG. 7 is a schematic perspective view of a further step of a method according to the present invention.
Figure 8:
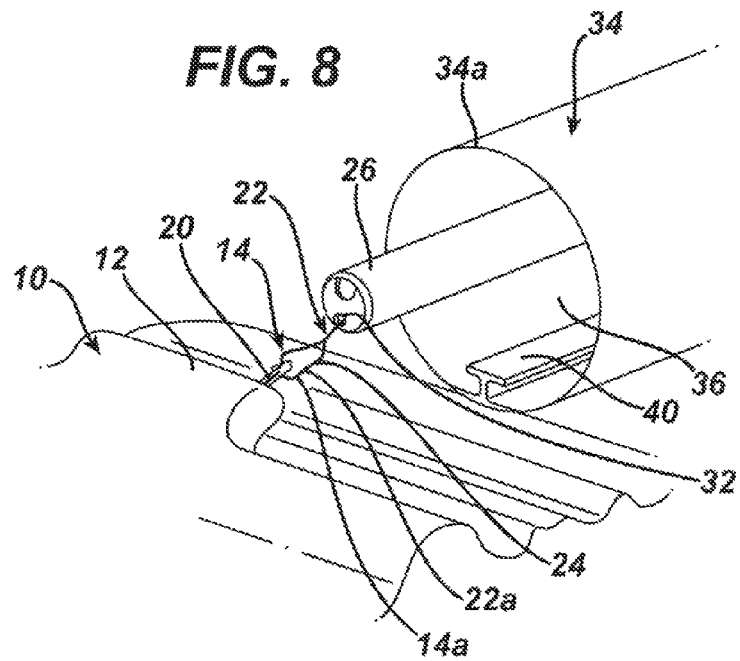
FIG. 8 is a schematic perspective view of a further step of a method according to the present invention.

The method according to the present invention preferably also comprises the step of withdrawing said grasping means 28 and said visualization device 26 after having fixed said means to the tissue to be excised (FIGS. 7 and 8).

According to a generic embodiment of the present invention, the present method also comprises the step of inserting said proximal portion of said traction means 14 into the window 18 of the surgical stapling device 16, outside of the patient's body, before introducing the surgical stapling device 16 into the patient's body. The surgical stapling device 16 is then guided by said traction means 14 whilst it is introduced into the patient's body (FIG. 9 with reference to the last step of the introduction of the surgical stapling device).

If the traction means 14 comprise at least one clip 20 connected to the suture 22, the last described step is carried out by inserting said proximal end of said suture 22 into the window 18 of said surgical stapling device 16, outside of the patient's body, before introducing said surgical stapling device 16 into the patient's body. In this case, the surgical stapling device 16 is guided by the suture 22 whilst said surgical stapling device 16 is introduced into the patient's body.

Figure 9:
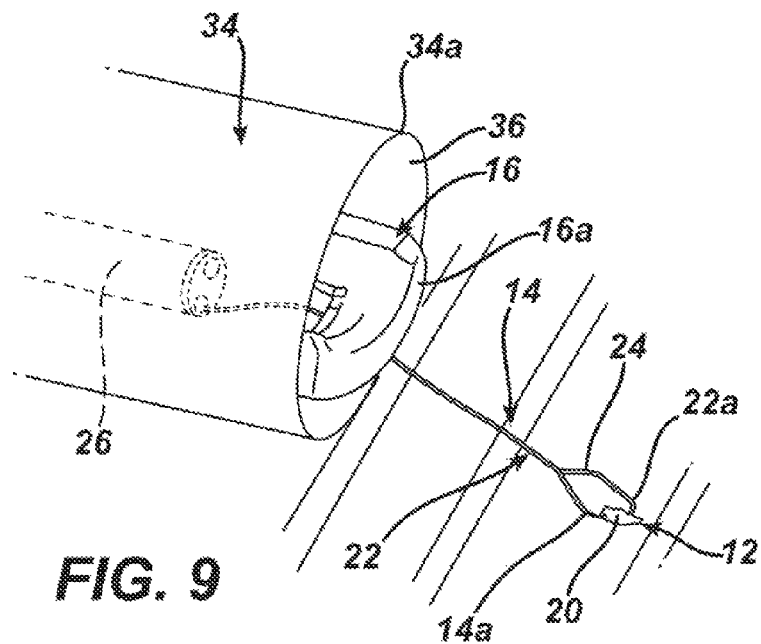
FIG. 9 is a schematic perspective view of a further step of a method according to the present invention.
Figure 10:
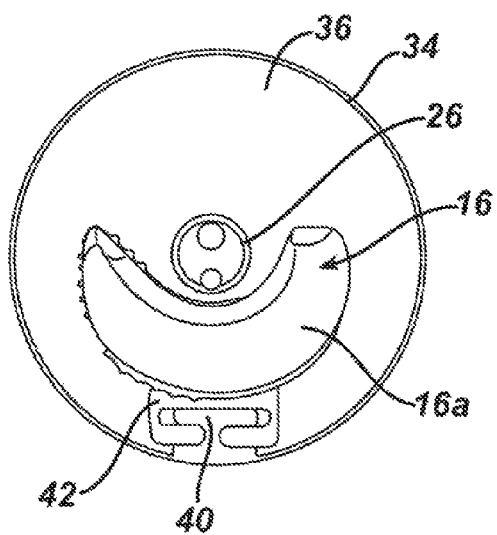
FIG. 10 is a front schematic view of a further step of a method according to the present invention.

Following FIGS. 7-8, the visualization device 26 and the grasping means 28 are withdrawn when the traction means have been fixed to the tissue to be excised. Then the suture 22 is inserted into the window 18 outside of the patient's body. The suture 22 can be re-inserted into the visualization device 26 that shall preferably be arranged in a concavity of the surgical stapling device. The visualization device 26 follows the surgical stapling device sliding on the suture (FIGS. 9 and 10). According to a different embodiment that is not illustrated, the suture can extend outside of the visualization device 26.

According to a generic embodiment of the invention, the present method can also comprise a first step of providing a sheath 34 having a distal end 34a and a proximal end 34b. Said sheath defines a work channel 36 for receiving in particular said traction means 14 and said surgical stapling device 16. Moreover, the sheath is particularly suitable for protecting the walls from perforations, in particular the walls of the colon when the present method is carried out endoluminally in order to excise a tissue sample of the colon. Moreover, said sheath 34 is introduced into the patient's body, positioning said distal end 34a of the sheath 34 close to the portion of the tissue to be excised 12, before fixing said traction means 14 to the tissue to be excised. An example of this embodiment has been shown in FIGS. 1-13, with reference to the first embodiment of the present invention. However, it can be used in different embodiments, for example having different types of traction means or different types of sheaths.

The sheath 34 is preferably made from flexible transparent material. The drawings show a schematic view of the sheath 34 after having been insufflated; however, it is possible to foresee a sheath of flexible material that naturally expands without insufflation when the devices, particularly the surgical stapling device and the visualization device, are introduced.

According to a generic embodiment of the invention, the sheath 34 is introduced into the patient's body by means of a visualization device that can be the same visualization device referred to as 26 and used in different steps of the present invention.

The visualization device 26 is introduced through the sheath 34, from the proximal end and to the distal end of the sheath, before introducing said sheath into the patient's body. The visualization device 26 has a distal end 26a and a proximal end.

Thereafter, the visualization device 26 is fixed to the sheath 34. The sheath 34 with the visualization device 26 is then introduced into the patient's body (FIG. 1).

Advantageously, the step of fixing the sheath to the visualization device can be carried out as follows. The visualization device 26 is introduced through the sheath 34 from the proximal end to the distal end of the sheath 34 by which the distal end of the visualization device comes out from the distal end of the sheath. Then the visualization device 26 is fixed to the sheath 34 placing an elastic connection sheath 38 on the distal end 34a of the sheath 34 and on the distal end 26a of the visualization device 26, before introducing said sheath 34 into the patient's body (FIG. 1).

Figure 2:
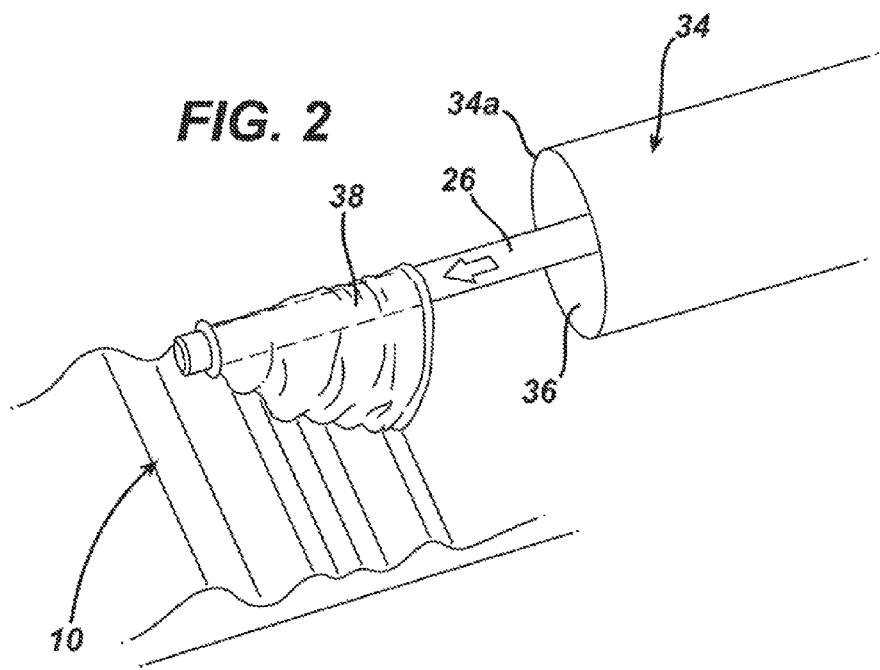
FIG. 2 is a schematic perspective view of a further step of the method according to the present invention.

According to an example of the present invention, the visualization device 26 is withdrawn from the sheath 34 before introducing said traction means 14 through the sheath 34 (FIGS. 2 and 3). By using an elastic connection sheath 38 to fix the sheath 34 to the visualization device 26, the step of withdrawing said visualization device 26 from the sheath 34 comprises the step of thrusting said visualization device 26, by which the distal end 26a of the visualization device 26 pulls the elastic connection sheath 38 from the distal end 34a of the sheath 34 (FIG. 2), and then the step of pulling said visualization device 26 associated with the sheath outside of said sheath (FIG. 3).

After the positioning of the sheath 34, the step of introducing said traction means 14 into the patient's body is carried out by introducing said traction means into the work channel 36 of said sheath 34, from the proximal end to the distal end of the sheath, before said traction means are fixed to the tissue to be excised (FIGS. 4-8). As stated above, the sheath can be insufflated or can be naturally expanded by introducing the necessary devices.

If the traction means comprise at least one clip 20 connected to the suture as described above and the step of introducing said at least one clip 20 into the patient's body and of fixing it to the tissue to be excised is carried out by grasping means 28, the grasping means are preferably introduced into the work channel 36 of said sheath 34 to grasp the tissue to be excised before fixing said clip to it. As described above, the ring 24 of the suture 22 is preferably arranged in the jaws 30 of said grasping means 28 and then said jaws 30 are closed around said ring 24 before introducing the grasping means 28 into the patient's body (FIG. 4), i.e. into the work channel 36 of said sheath 34, and before fixing said at least one clip 20 to the tissue to be excised (FIG. 6). Preferably the step of introducing said traction means 14 into the patient's body comprise the step of inserting said grasping means 28 through a visualization device outside of the patient's body, and then of introducing said visualization device and said grasping means 28 into the work channel 36 of said sheath 34 to fix said traction means to the tissue to be excised (FIG. 5). The visualization device can be the same visualization device for all of the steps, i.e. the visualization device referred to as 26 in the drawings. Preferably, the suture 22 is slotted into a channel 32 of said visualization device 26 before introducing said visualization device 26 and said grasping means 28 into the work channel 36 of said sheath 34 by which the proximal end of the suture 22 extends outside of the visualization device 26 and of the patient's body (FIG. 5). In a different embodiment that is not illustrated, the suture 22 extends along the outside of the visualization device 26 before introducing said visualization device 26 and said grasping means 28 into the work channel 36 of said sheath 34.

Preferably, said grasping means 28 and said visualization device are withdrawn from the sheath before inserting said surgical stapling device.

According to a possible embodiment (not shown), the suture is inserted into the patient's body before introducing said grasping means. The grasping means grasp the distal end of the suture before fixing the at least one clip to the tissue to be excised. In particular, the suture can be fixed to the sheath during the introduction of the sheath into the patient's body.

According to an embodiment of the invention in which the sheath 34 is introduced into the patient's body, the step of introducing said surgical stapling device 16 into the patient's body is generically carried out by inserting said surgical stapling device 16 through the sheath 34, into the work channel 36, from the proximal end 34b to the distal end 34a of the sheath 34, before pulling the tissue to be excised through said window 18 of the surgical stapling device 16 and before cutting the tissue pulled through said window 18.

Preferably, the step of introducing said surgical stapling device 16 into the patient's body is carried out by guiding said surgical stapling device 16 inside the work channel 36 of the sheath 34. The surgical stapling device 16 is for example guided in the work channel 36 sliding along a track 40 of the sheath 34, the track extending longitudinally along the sheath. Particularly, the surgical stapling device 16 comprises an extension 42 suitable for coupling with the track 40 in order to radially exert a restriction for the surgical stapling device 16 with respect to the sheath 34.

Even when the surgical stapling device 16 is guided by the sheath 34 as described above, the proximal portion of said traction means 14 is inserted into the window 18 of the surgical stapling device 16, outside of the patient's body, before introducing said surgical stapling device into said sheath. Thus, the surgical stapling device 16 is further guided by said traction means 14 whilst said surgical stapling device 16 is introduced through said sheath 34.

In particular, a preferred embodiment of the present invention can be carried out as follows (FIGS. 1-13).

The first steps of the method according to the present invention comprise the steps of:

providing traction means 14 having a distal end 14a suitable for being fixed to at least one portion of tissue to be excised and a proximal portion, providing a surgical stapling device 16 having a distal end 16a with a window 18 for receiving the tissue to be excised and comprising cutting and stapling means operating through said window, providing a sheath 34 having a distal end 34a and a proximal end 34b and defining a work channel 36 to receive said traction means 14 and said surgical stapling device 16.

Then the method is carried out, as shown in FIG. 1, according to the following steps:

introducing a visualization device 26 through the sheath 34 from the proximal end to the distal end of the sheath, before introducing said sheath into the patient's body, fixing the visualization device 26 to the sheath 34 and introducing said sheath with the visualization device into the patient's body, said distal end of said sheath being positioned close to the portion of tissue to be excised (FIG. 1), and withdrawing the visualization device 26 from the sheath 34 (FIGS. 2-3).

These last steps can be carried out as described above, using an elastic connection sheath 38 as shown in FIGS. 1-3.

Then the method is carried out as shown in FIGS. 4-7, according to the following steps:

inserting said traction means 14 through the sheath 34, inside the work channel 36, from the proximal end to the distal end of the sheath, and fixing said traction means 14 to the at least one portion of tissue to be excised.

In particular, as described earlier, said distal portion 14a of said traction means 14 comprises at least one clip 20 by which the step of fixing said distal portion of said traction means to the at least one portion of tissue to be excised is carried out by fixing said at least one clip 20 of said traction means to the tissue to be excised. Said clip 20 is connected to the distal end of a suture 22 of said traction means 14 to pull the tissue through said window 18, said suture extending between said distal end 22a and a proximal end corresponding to the proximal portion of said traction means. The step of introducing said at least one clip 20 into the patient's body and of fixing it to the tissue to be excised is preferably carried out by means of grasping means 28 that grasp the tissue before fixing said clip to it. More preferably the step of introducing said traction means 14 into the patient's body comprises the step of inserting said grasping means 28 through a visualization device 26 outside of the patient's body, and then introducing said visualization device 26 and said grasping means 28 through the work channel 36, from the proximal end to the distal end of the sheath 34. The grasping means 28 and the visualization device 26 are then withdrawn from the patient's body, leaving the suture in the sheath with the clip fixed to the tissue to be excised.

Then the method comprises the step of inserting said proximal end of said suture into the window 18 of said surgical stapling device, outside of the patient's body, before introducing said surgical stapling device 16 into said sheath 34. Preferably the proximal end of the suture 22 is re-inserted into the visualization device 26 and the visualization device 26 is arranged in a concavity of the surgical stapling device.

Figure 11:
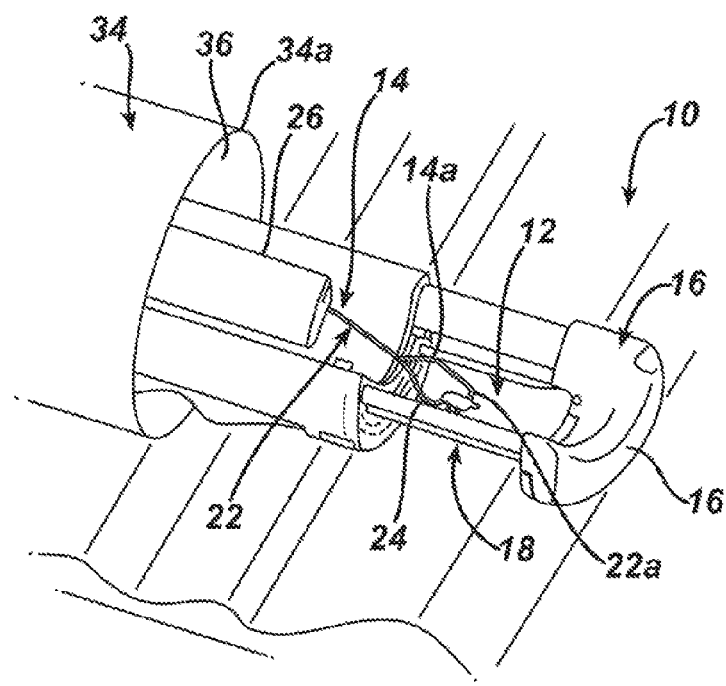
FIG. 11 is a schematic perspective view of a further step of a method according to the present invention.
Figure 12:
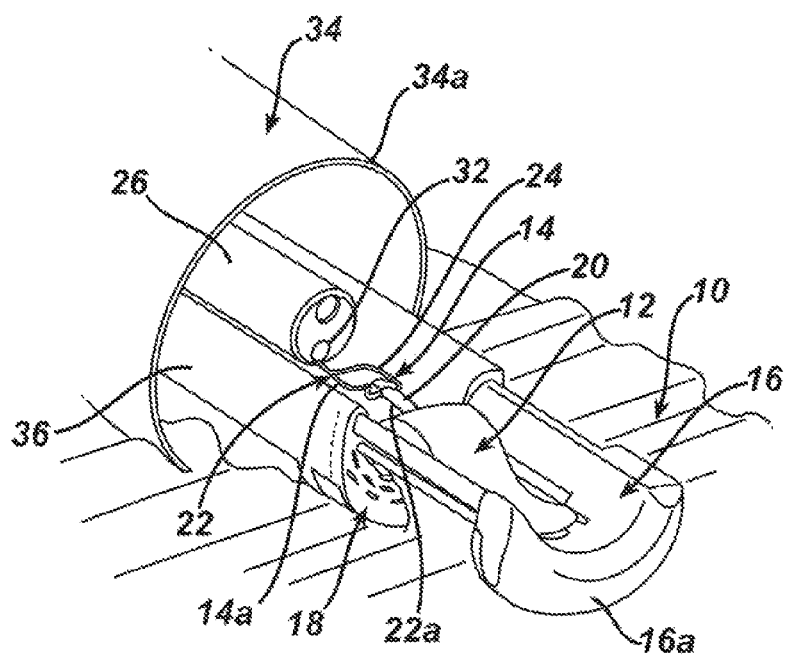
FIG. 12 is a schematic perspective view of a further step of the method according to the present invention.

The method also comprises the steps of:

inserting said surgical stapling device 16 through the work channel 36 of said sheath 34, sliding on the suture from the proximal end to the distal end of the sheath, whilst the visualization device follows the surgical stapling device, and positioning said distal end of the surgical stapling device close to the tissue to be excised (FIGS. 9-11).

Preferably, said surgical stapling device 16 is also guided inside the work channel 36 sliding along a track 40 of the sheath 34.

Figure 13:
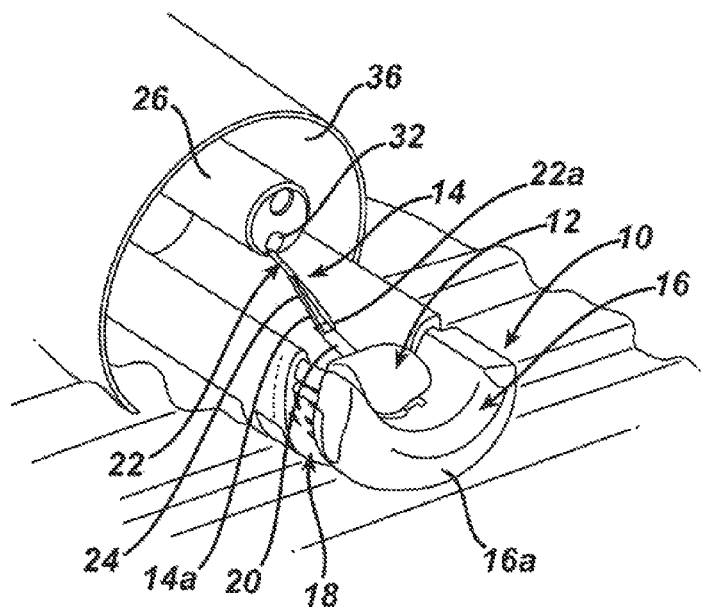
FIGS. 13 and 13A are schematic perspective views of alternative further steps of the method according to the present invention.
Figure 13A:
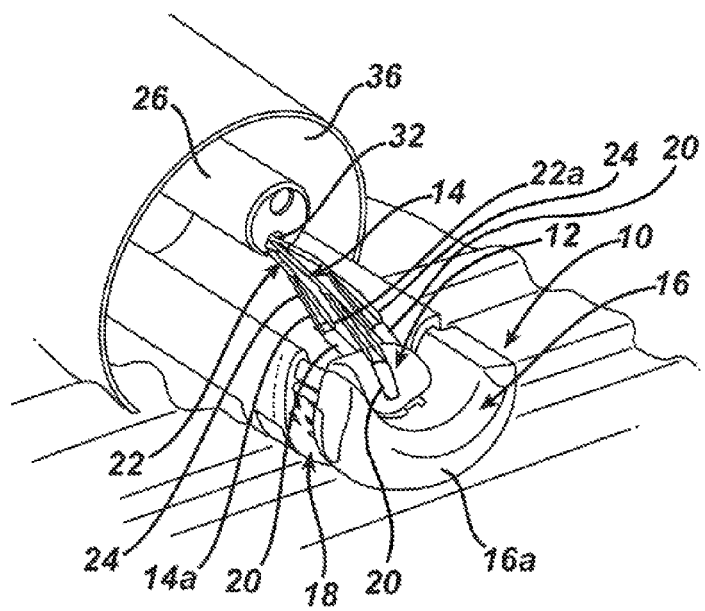

Finally, the method comprises the steps of:

exerting a traction on said traction means 14 by which an appropriate amount of tissue is pulled through said window 18 (FIG. 12), and cutting and stapling said tissue by actuating said cutting and stapling means of said surgical stapling device 16 through said window 18 (FIG. 13).

Than all of the devices are withdrawn from the patient's body and the excised sample is taken out by means of the traction means.

The method described earlier is particularly suitable for being carried out according to an endoluminal approach, using natural or artificial orifices. However, the method described can also be carried out according to a laparoscopic approach.

FIGS. 14-23 show a further embodiment of the present invention, as generically described earlier. The method described is suitable both for an endoluminal approach and for a laparoscopic approach. As stated above, the visualization device is a generic device, in particular an endoscope in the case of an endoluminal approach.

In accordance with this embodiment, the method comprises the step of providing a sheath 44 having a distal end 44*a* and a proximal end 44*b*. The sheath 44 defines a first work channel 46 and a second work channel 48. The first work channel 46 is suitable for receiving said traction means 14 and said surgical stapling device 16, the second work channel 48 is suitable for receiving a visualization device 50.

The sheath is preferably made from flexible transparent material. The drawings show a schematic view of the sheath 44 after having been insufflated; however, it is possible to foresee a sheath of flexible material that expands naturally without insufflation when the devices, particularly the surgical stapling device and the visualization device, are introduced.

Figure 14:
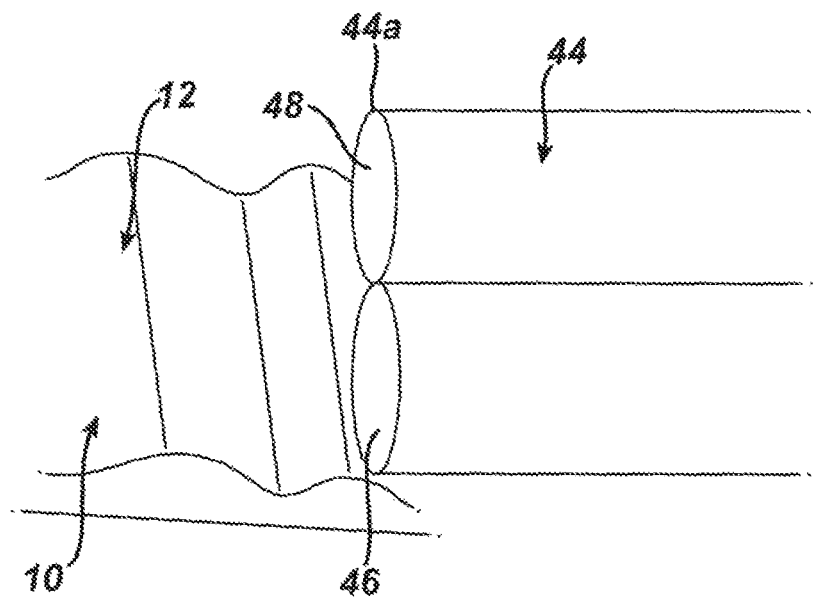
FIG. 14 is a schematic perspective view of a step of a further embodiment of a method for endoluminally or laparoscopically excising a tissue sample from areas in a patient's body according to the present invention.

Then the sheath 44 is introduced into the patient's body and the distal end 44*a* of the sheath 44 is positioned close to the portion of tissue to be excised before fixing said traction means 14 to the tissue to be excised 12 (FIG. 14). Advantageously, the sheath 44 is introduced into the patient's body by means of a visualization device (the visualization device 50 can be used for different steps of the present method).

Figure 18:
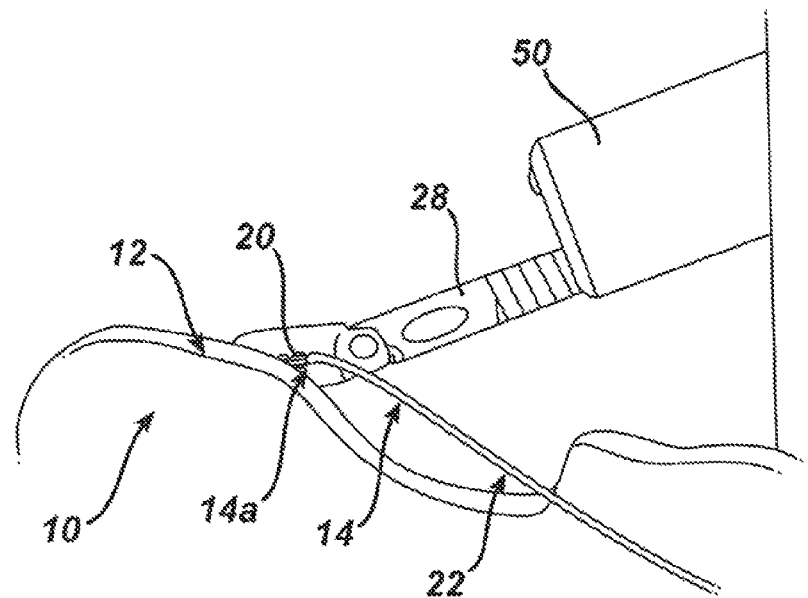
Figure 19:
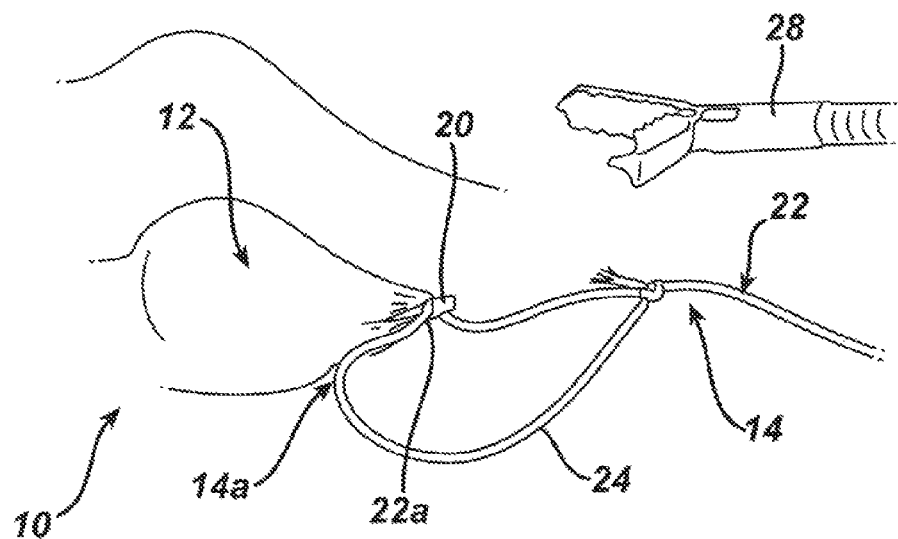

Also in this case, said distal portion 14*a* of said traction means 14 comprises at least one clip 20 by which the step of fixing said distal portion 14*a* of said traction means 14 to the at least one portion of tissue to be excised is carried out by fixing said at least one clip 20 of said traction means 14 to the tissue to be excised (FIG. 18). As described in the previous embodiment, the clip 20 is connected to the distal end 22*a* of the suture 22 of said traction means 14 to pull the tissue through said window 18. The suture 22 extends between said distal end 22*a* and a proximal end 22*b* corresponding to a proximal portion 14*b* of said traction means 14.

Figure 15:
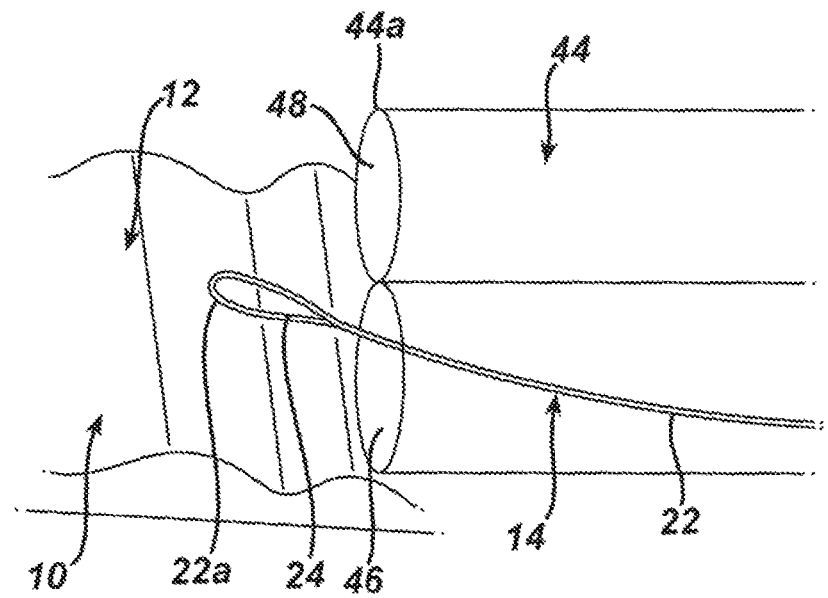
FIGS. 15-23 are schematic perspective view of further steps of the method according to the present invention.

As shown in FIG. 15, said suture 22 is introduced into said first work channel 46 of said sheath 44.

According to an embodiment of the invention, not illustrated, the suture 22 is fixed inside said first work channel 46 whilst said sheath 44 is introduced into the patient's body. The distal end 22*a* of said suture 22 extends from the distal end 44*a* of the sheath 44.

According to a different embodiment, shown in FIGS. 1-2, said suture 22 is introduced through said first work channel 46 after having introduced said sheath 44 into the patient's body. Also in this case the distal end 22*a* of said suture 22 extends from the distal end 44*a* of the sheath 44. According to a possible embodiment, said suture 22 is introduced through said first work channel 46 by means of positioning grasping means or by means of a visualization device (not shown).

Figure 16:
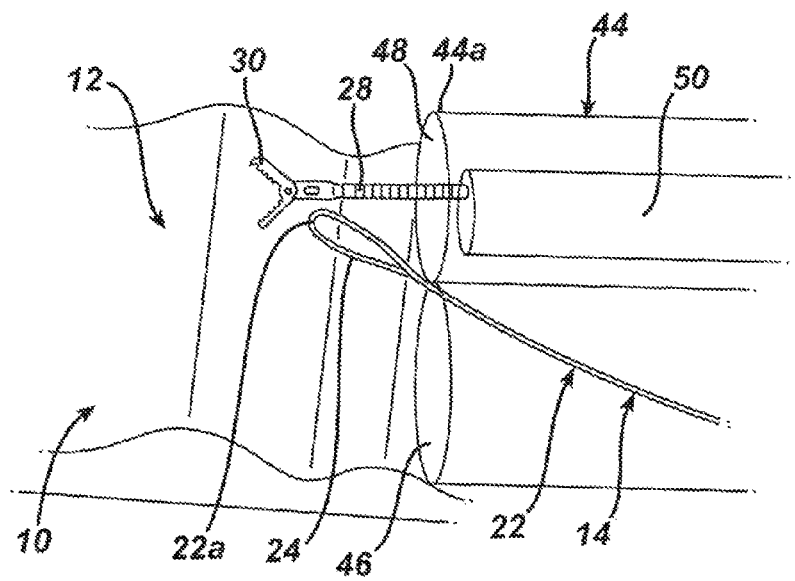
Figure 17:
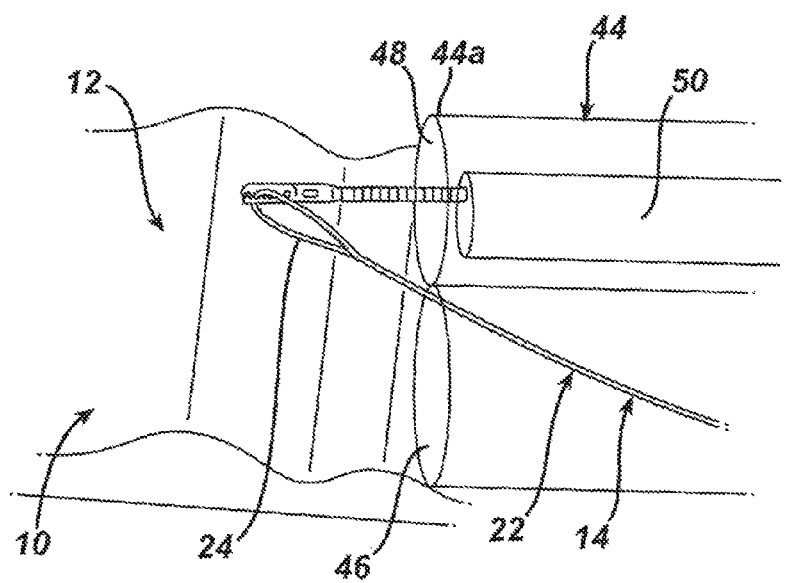

If the traction means comprise at least one clip 20, the step of introducing said at least one clip 20 into the patient's body and of fixing it to the tissue to be excised is carried out by means of grasping means 28 that are preferably introduced through said sheath 44 (FIG. 16). Said grasping means 28 grasp said distal end 22*a* of the suture inside the patient's body. Then the grasping means 28 grasp the tissue to be excised 12 before fixing said clip 20 to it. Preferably said grasping means 28 are inserted through said visualization device 50. The visualization device 50 with the grasping means 28 are inserted inside said second work channel 48 (FIGS. 16 and 17).

Figure 20:
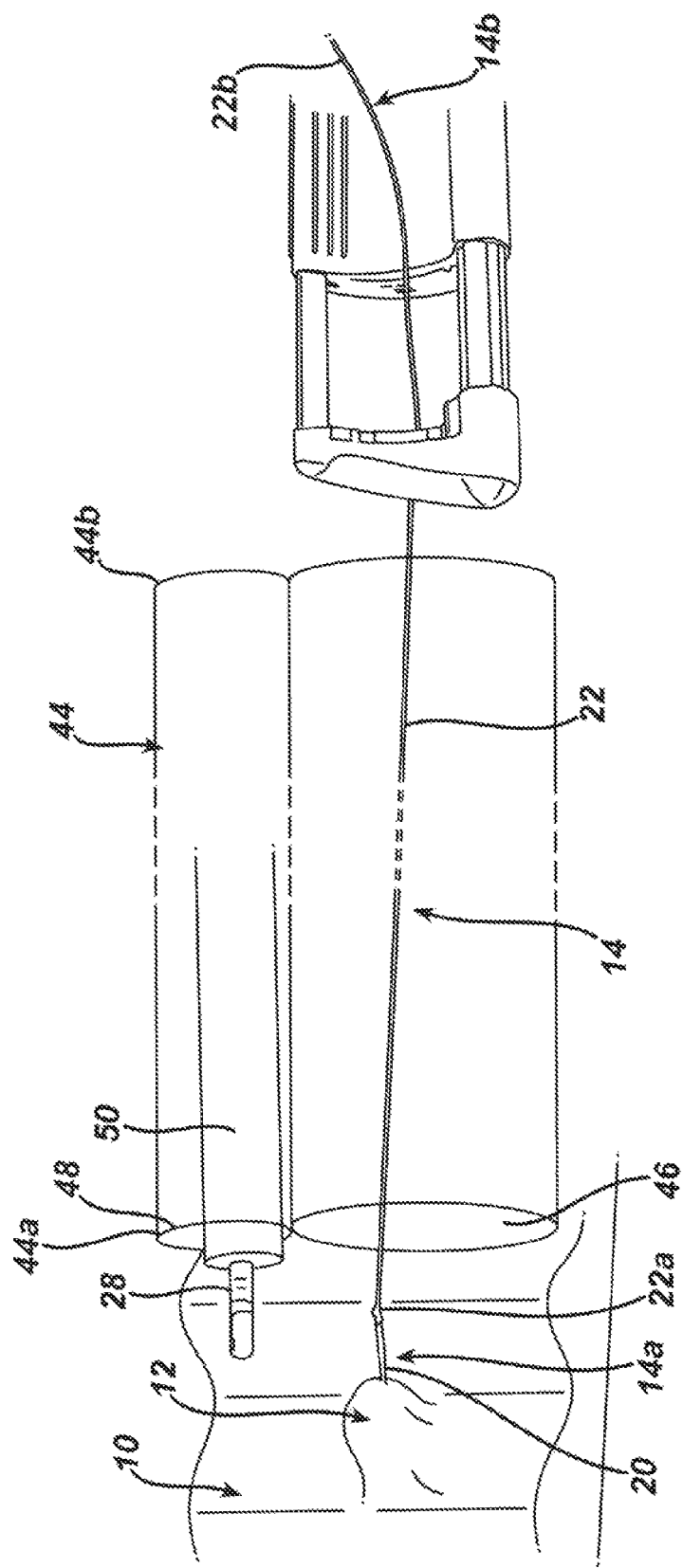
Figure 21:
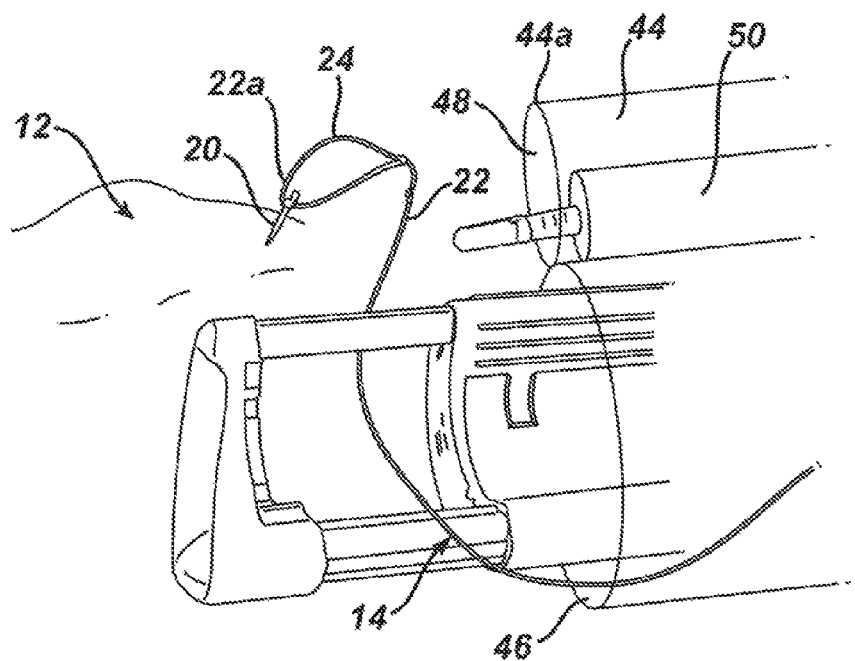

After the clip has been fixed to the tissue to be excised, said proximal end 22*b* of said suture 22 is inserted into the window 18 of said surgical stapling device 16, outside of the patient's body, before said surgical stapling device 16 is introduced through said first work channel 46 of said sheath 44, by which said surgical stapling device 16 is guided by said suture 22 (FIG. 20).

The insertion of the surgical stapling device can be carried out under the visual control of the visualization device 50, or else it is possible to insert the suture 22 into a different visualization device, after having introduced a proximal end of the suture into the window 18 of the surgical stapling device 16, outside of the patient's body. The visualization device shall preferably be arranged in a concavity of the surgical stapling device and shall follow the surgical stapling device 16 through the sheath sliding on the suture inside the first work channel. According to a different embodiment that is not illustrated, the suture can extend outside of the visualization device.

The surgical stapling device reaches the tissue to be excised (FIG. 21) and the tissue is pulled through the window (FIGS. 22 and 23). During the step of pulling said suture, said proximal end 22*b* of the suture 22 can be pulled directly from outside of the patient or else it can be pulled by grasping means (FIGS. 22 and 23). The grasping means 28 can be the same ones used to fix the clip. They can be arranged in the second work channel or else they can be inserted directly in the first work channel.

The tissue pulled by the traction means is then cut and stapled by actuating said cutting and stapling means of said surgical stapling device 16 through said window 18 (FIG. 23). Finally, all of the devices are withdrawn from the patient's body and the tissue sample fixed to the suture is taken out.

As an example, this further embodiment can be carried out as follows. The first steps comprise the steps of:

providing traction means 14 having a distal portion 14*a* suitable for being fixed to at least one portion of the tissue to be excised and a proximal portion 14*b*, foreseeing a surgical stapling device 16 having a distal end 16*a* with a window 18 for receiving the tissue to be excised and comprising cutting and stapling means operating through said window 18, providing a sheath 44 having a distal end 44*a* and a proximal end 44*b* and defining a first work channel 46 and a second work channel 48. Said first work channel 46 is suitable for receiving said traction means 14 and said surgical stapling device 16; said second work channel 48 is suitable for receiving said visualization device 50.

Said visualization device 50 is inserted through said second work channel 48 of said sheath 44 from a proximal end 44*b* to a distal end 44*a* of the sheath, before inserting said sheath into the patient's body. In particular, the visualization device 50 is fixed to the sheath 44 and said sheath with the visualization device 50 is then introduced into the patient's body, said distal end of the sheath being positioned close to the portion of tissue to be excised. Then the visualization device 50 is withdrawn from the sheath.

The following steps of the method comprise:

inserting said traction means through said first work channel 46 of said sheath 44, from the proximal end to the distal end of the sheath, and fixing said traction means 14 to the at least one portion of the tissue to be excised.

Said distal portion of said traction means comprises at least one clip 20 by which the step of fixing said distal portion of said traction means to at least one portion of the tissue to be excised is carried out by fixing said at least one clip of said traction means to the tissue to be excised. Said clip is connected to a distal end 22*a* of a suture 22 of said traction means 14 to pull the tissue through said window 18 (said suture extends between said distal end 22*a* and a proximal end 22*b* corresponding to the proximal portion 14b of said traction means 14). Said suture 22 of said traction means 14 can be inserted through said first work channel 46 of said sheath 44 and fixed to it, from the proximal end to the distal end of the sheath, before introducing said sheath into the patient's body. Alternatively, said suture 22 of said traction means 14 is inserted through said first work channel 46 of said sheath 44, from the proximal end to the distal end of the sheath introduced into the patient's body (FIG. 15).

The step of introducing said at least one clip 20 into the patient's body and of fixing it to the tissue to be excised is carried out by means of grasping means 28 that grasp the tissue before fixing said clip to it. Said grasping means 28 can be inserted through a visualization device 50 outside of the patient's body, by which said visualization device 50 and said grasping means 28 are then introduced through said second work channel 48, from the proximal end to the distal end of the sheath.

Jaws 30 of the grasping means 28 grasp the distal end 22a of the suture 22 (in particular a ring formed at the distal end 22a of the suture 22) inside the patient's body. Then the grasping means 28 grasp the tissue and fix the clip to it.

The following steps of the method comprise:

inserting said proximal end 22b of said suture 22 into the window 18 of said surgical stapling device 16, outside of the patient's body, before introducing said surgical stapling device 16 into the sheath 44 (FIG. 20), inserting said surgical stapling device 16 through said first work channel 46 of said sheath 44, from the proximal end to the distal end of the sheath, and positioning said distal end of the surgical stapling device 16 close to the tissue to be excised (FIGS. 21 and 22); said surgical stapling device is preferably guided inside the first work channel sliding along a track of the sheath, exerting a traction on said traction means 14 by which an appropriate amount of tissue is pulled through said window 18 (FIG. 22), and cutting and stapling said tissue by actuating said cutting and stapling means of said surgical stapling device 16 through said window 18 (FIG. 23).

After having introduced the proximal end 22b of the suture 22 into the window 18, the proximal end 22b of the suture 22 can be inserted into a visualization device suitable for being arranged in a concavity of the surgical stapling device 16. The visualization device shall follow the surgical stapling device during introduction through the sheath.

With reference to all of the embodiments described, the step of fixing said traction means 14 to at least one portion of the tissue to be excised 12 can comprise the step of fixing a plurality of clips 20 of said traction means to the tissue to be excised. Each clip 20 of said plurality of clips is connected to a suture 22 to pull the tissue through said window 18. All of the sutures are inserted into the window 18.

According to a possible embodiment, said clips are fixed along a border of the portion of tissue to be excised. Alternatively, at least one clip 20 of said plurality of clips is fixed directly to the portion of tissue to be excised.

With reference to all of the embodiments described, the method according to the present invention can comprise the step of highlighting the tissue to be excised through marks or tattoos and, whilst a traction is exerted on said traction means, of monitoring the amount of tissue pulled through the window 18 of the surgical stapling device 16 checking the position of said marks or of said tattoos.

Preferably, in all of the embodiments described, the surgical stapling device is in an open configuration when it is outside of the patient's body (the window 18 is open and preferably has greater dimensions). This configuration allows easy introduction of the suture through the window 18. Then the window is closed so that the stapling device is in a closed configuration whilst it is introduced through the sheath (or generically into the patient's body). This configuration is less invasive. Then when the surgical stapling device reaches the tissue to be cut, the window 18 is reopened in order to cut and staple the tissue.

More advantageously, the surgical stapling device comprises an elongated structure, not shown, connected to a handle. The elongated structure is preferably flexible.

In accordance with a further aspect, the present invention concerns traction means 14 for excising a tissue sample comprising a distal portion 14a, comprising at least one clip 20 suitable for being fixed to at least one portion 12 of tissue to be excised, and a proximal portion 14b suitable for being subjected to traction.

Preferably, said at least one clip 20 is suitable for being connected to a distal end 22a of a suture 22 to pull the tissue to be excised. The suture 22 extends between said distal end 22a and a proximal end 22b corresponding to the proximal portion of said traction means 14.

In accordance with a possible embodiment, said at least one clip 20 is connected to a ring 24 formed at a distal end 24a of said suture 22 to pull the tissue to be excised.

Advantageously, grasping means 28 are foreseen that are suitable for grasping and pulling said proximal end of the suture 22. Moreover, a visualization device can be foreseen that is suitable for receiving a portion of said suture 22 that extends through a channel of said visualization device 26 or else suitable for cooperating with a portion of said suture 22 that extends along an outer surface of a visualization device 26.

In accordance with a possible embodiment, grasping means 28 are foreseen that are suitable for fixing said clip 20 to the at least one portion of tissue to be excised and for connected said clip to said suture 22.

According to yet another aspect, the present invention concerns a kit for endoluminally or laparoscopically excising a tissue sample from areas in a patient's body comprising traction means 14, for example as described above, and a surgical stapling device 16 having a distal end 16a with a window 18 for receiving the tissue to be excised 12 and comprising cutting and stapling means that act through said window 18. The traction means are suitable for being inserted through said window 18 starting from a proximal portion 14b of the traction means themselves.

In accordance with a possible embodiment, the kit also comprises a sheath 34 having a distal end 34a and a proximal end 34b. Said sheath defines a work channel 36 for receiving the traction means 14 and the surgical stapling device 16.

In accordance with a different embodiment the kit comprises a sheath 44 having a distal end 44a and a proximal end 44b, in which said sheath 44 defines a first work channel 46 and a second work channel 48. The first work channel 46 is suitable for receiving the traction means 14 and the surgical stapling device 16; the second work channel 48 is suitable for receiving a visualization device 50.

Preferably, the sheath is made from flexible transparent material suitable for being insufflated or else suitable for being naturally widened through the insertion of the devices (traction means, stapling device, visualization devices, . . . )

In accordance with a possible embodiment, said sheath comprises a track 40 that extends longitudinally along the sheath itself and the surgical stapling device 16 is suitable for sliding inside the sheath along said track. Preferably, the surgical stapling device 16 comprises an extension 42 suitable for coupling with the track 40 in order to radially exert a restriction for the surgical stapling device 16 with respect to the sheath 34.

In accordance with a possible embodiment, the kit according to the present invention also comprises an elastic connection sheath 38 suitable for slotting onto the distal end 34*a* of the sheath 34 and onto a distal end 26*a* of a visualization device 26 to connect them in the insertion step.

From the above description, it is clear that an improved method for endoluminally or laparoscopically excising a tissue sample is foreseen, having a specific amount and volume, from areas in a patient's body. Traction means and a kit are also foreseen that allow precise and safe traction of the tissue. Even if the aforementioned invention has been described in detail for the sake of clarity, it is obvious that modifications can be made without departing from the attached claims.

The invention claimed is:

1. A method for endoluminally or laparoscopically excising a tissue sample from areas in a patient's body, the method comprising the steps of:
    providing traction means (14) having a distal portion (14*a*) suitable for being fixed to at least one portion (12) of the tissue to be excised and a proximal portion,
    introducing said distal portion (14*a*) of said traction means (14) into the patient's body and positioning said distal portion (14*a*) of said traction means (14) close to the tissue to be excised (12), by which at least one portion of said traction means (14) that extends from said distal portion (14*a*) is positioned in the patient's body,
    fixing said distal portion (14*a*) of said traction means (14) to at least one portion of tissue to be excised (12),
    providing a surgical stapling device (16) having a distal end (16*a*) with a window (18) for receiving the tissue to be excised (12) and comprising cutting and stapling means that act through said window (18),
    introducing said surgical stapling device (16) into the patient's body and positioning said distal end (16*a*) of the surgical stapling device close to the tissue to be excised (12),
    exerting a traction on said traction means (14) by which an amount of tissue is pulled through said window (18),
    cutting and stapling said tissue by actuating said cutting and stapling means of said surgical stapling device (16) through said window (18),
    wherein the step of providing the traction means comprises:
        forming a ring (24) at a distal end (22*a*) of a suture (22), said ring (24) defining an eyelet, and connecting a clip (20) to said ring (24), wherein said suture (22), ring (24) and clip (20) form said fraction means,
    wherein the step of introducing said distal portion (14*a*) of said traction means (14) into the patient's body comprises:
        positioning the ring (24) of the suture (22) between jaws of a grasping means (28) with one jaw of said jaws hooking into said eyelet,
        introducing the grasping means (28) hooked into the eyelet of the ring (24) into the patient's body,
    wherein the step of fixing said distal portion (14*a*) of said traction means (14) to the portion of tissue to be excised comprises grasping the tissue by means of said grasping means (28) and then fixing said clip to the tissue by means of said grasping means (28).

2. A method for endoluminally or laparoscopically excising a tissue sample from areas in a patient's body according to claim 1, in which said suture is extended between said distal end (22*a*) and a proximal end (22*b*) corresponding to the proximal portion (14*b*) of said traction means (14).

3. A method for endoluminally or laparoscopically excising a tissue sample from areas in a patient's body according to claim 2, in which the step of exerting a traction on said traction means (14) comprises the step of pulling said proximal end (22*b*) of the suture (22) from outside of the patient's body.

4. A method for endoluminally or laparoscopically excising a tissue sample from areas in a patient's body according to claim 3, in which the step of exerting a traction on said traction means (14) is carried out under the visual control of a visualization device.

5. A method for endoluminally or laparoscopically excising a tissue sample from areas in a patient's body according to claim 4, in which, during the step of exerting a traction on said traction means (14), a portion of said suture (22) extends through said visualization device, said proximal end of the suture coming out from a proximal end of the visualization device and said distal end of the suture coming out from a distal end of the visualization device.

6. A method for endoluminally or laparoscopically excising a tissue sample from areas in a patient's body according to claim 2, in which the step of exerting a traction on said traction means (14) comprises the step of pulling said suture by means of said grasping means (28).

7. A method for endoluminally or laparoscopically excising a tissue sample from areas in a patient's body according to claim 6, in which the step of exerting a traction on said traction means (14) is carried out under the visual control of a visualization device.

8. A method for endoluminally or laparoscopically excising a tissue sample from areas in a patient's body according to claim 2, in which a step of introducing said clip (20) into the patient's body and said step of fixing said clip to the tissue to be excised is carried out by means of said grasping means that grasp the tissue before fixing the clip to said tissue.

9. A method for endoluminally or laparoscopically excising a tissue sample from areas in a patient's body according to claim 8, in which said clip and said suture are introduced into the patient's body by means of said grasping means (28).

10. A method for endoluminally or laparoscopically excising a tissue sample from areas in a patient's body according to claim 9, in which jaws (30) of said grasping means (28) grasp the distal end (22*a*) of the suture (22) before introducing the grasping means into the patient's body and before fixing said at least one clip to the tissue to be excised.

11. A method for endoluminally or laparoscopically excising a tissue sample from areas in a patient's body according to claim 10, in which, during the step of grasping the distal end (22*a*) of the suture (22), a ring (24) formed at the distal end of the suture (22) is positioned in said jaws of the grasping means, and the jaws are closed around said ring before introducing said grasping means into the patient's body and before fixing said at least one clip to the tissue to be excised.

12. A method for endoluminally or laparoscopically excising a tissue sample from areas in a patient's body according to claim 8, in which the step of introducing said at least one clip (20) into the patient's body and of fixing said clip to the tissue to be excised is carried out under the control of a visualization device.

13. A method for endoluminally or laparoscopically excising a tissue sample from areas in a patient's body according to claim 12, in which the step of introducing said traction means into the patient's body comprises the step of inserting said grasping means through said visualization device outside of the patient's body, and then of introducing said visualization device and said grasping means into the patient's body to fix said traction means to the tissue to be excised.

14. A method for endoluminally or laparoscopically excising a tissue sample from areas in a patient's body according to claim 13, in which said suture is inserted in a channel (32) of the visualization device before introducing said visualization device and said grasping means into the patient's body, the proximal end (22*b*) of the suture (22) extending outside of the visualization device and of the patient's body.

15. A method for endoluminally or laparoscopically excising a tissue sample from areas in a patient's body according to claim 13, also comprising the step of withdrawing said grasping means and said visualization device after having fixed said traction means to the tissue to be excised.

16. A method for endoluminally or laparoscopically excising a tissue sample from areas in a patient's body according to claim 2, also comprising the step of inserting said proximal end of said suture into the window (18) of the surgical stapling device, outside of the patient's body, before introducing said surgical stapling device into the patient's body.

17. A method for endoluminally or laparoscopically excising a tissue sample from areas in a patient's body according to claim 16, in which said surgical stapling device is guided by said suture whilst said surgical stapling device is introduced into the patient's body.

18. A method for endoluminally or laparoscopically excising a tissue sample from areas in a patient's body according to claim 16, in which said proximal end of said suture is inserted through or extended outside a visualization device, the visualization device following said surgical stapling device during introduction into the patient's body.

19. A method for endoluminally or laparoscopically excising a tissue sample from areas in a patient's body according to claim 18, in which said visualization device is arranged in a concavity of said surgical stapling device.

20. A method for endoluminally or laparoscopically excising a tissue sample from areas in a patient's body according to claim 2, in which the step of fixing said traction means to at least one portion of tissue to be excised comprises the step of fixing a plurality of clips (20) of said traction means to the tissue to be excised, each clip of said plurality of clips being connected to a suture to pull the tissue through said window.

21. A method for endoluminally or laparoscopically excising a tissue sample from areas in a patient's body according to claim 20, in which said plurality of clips (20) are fixed along a border of the portion of the tissue to be excised.

22. A method for endoluminally or laparoscopically excising a tissue sample from areas in a patient's body according to claim 20, in which at least one clip of said plurality of clips (20) is fixed directly to the portion of the tissue to be excised.

23. A method for endoluminally or laparoscopically excising a tissue sample from areas in a patient's body according to claim 1, also comprising the step of inserting said proximal portion of said traction means into the window (18) of the surgical stapling device (16), outside of the patient's body, before introducing said surgical stapling device into the patient's body.

24. A method for endoluminally or laparoscopically excising a tissue sample from areas in a patient's body according to claim 23, in which said surgical stapling device is guided by said traction means (14) whilst said surgical stapling device is introduced into the patient's body.

25. A method for endoluminally or laparoscopically excising a tissue sample from areas in a patient's body according to claim 1, also comprising the steps of:

providing a sheath (34) having a distal end (34*a*) and a proximal end (34*b*), said sheath defining a work channel (36) to receive said traction means (14) and said surgical stapling device (16) and to protect the walls from perforation, introducing said sheath into the patient's body and positioning said distal end close to the portion of tissue to be excised before fixing said traction means to the tissue to be excised.

26. A method for endoluminally or laparoscopically excising a tissue sample from areas in a patient's body according to claim 25, also comprising the steps of:

introducing a visualization device through the sheath, from the proximal end to the distal end of the sheath, before introducing said sheath into the patient's body, said visualization device having a proximal end and a distal end, fixing the visualization device to the sheath and introducing said sheath with the visualization device into the patient's body.

27. A method for endoluminally or laparoscopically excising a tissue sample from areas in a patient's body according to claim 26, in which said visualization device is introduced through the sheath from the proximal end to the distal end of the sheath by which the distal end of the visualization device comes out from the distal end of the sheath, and in which said visualization device is fixed to the sheath placing an elastic connection sheath on the distal end of the sheath and on the distal end of the visualization device, before introducing said sheath into the patient's body.

28. A method for endoluminally or laparoscopically excising a tissue sample from areas in a patient's body according to claim 26, in which said visualization device is withdrawn from the sheath before introducing said traction means (14) through said sheath.

29. A method for endoluminally or laparoscopically excising a tissue sample from areas in a patient's body according to claim 28, in which the step of withdrawing said visualization device from said sheath comprises the step of thrusting said visualization device by which the distal end of the visualization device pulls the elastic connection sheath from the distal end of the sheath and then the step of pulling said visualization device outside of said sheath.

30. A method for endoluminally or laparoscopically excising a tissue sample from areas in a patient's body according to claim 25, in which the step of introducing said traction means into the patient's body is carried out by introducing said traction means into the work channel (36) of the sheath (34), from the proximal end to the distal end of the sheath, before fixing said traction means to the tissue to be excised.

31. A method for endoluminally or laparoscopically excising a tissue sample from areas in a patient's body according to claim 30, in which said clip attached to said suture is introduced into the patient's body and fixed to the tissue to be excised by means of said grasping means that are inserted into the work channel of said sheath.

32. A method for endoluminally or laparoscopically excising a tissue sample from areas in a patient's body according to claim 31, in which said clip and said suture are introduced into the work channel of said sheath by means of said grasping means.

33. A method for endoluminally or laparoscopically excising a tissue sample from areas in a patient's body according to claim 32, in which jaws of said grasping means grasp the distal end of the suture before the grasping means are introduced into the work channel of the sheath and before fixing said at least one clip to the tissue to be excised.

34. A method for endoluminally or laparoscopically excising a tissue sample from areas in a patient's body according to claim 33, in which, during the step of grasping the distal end of the suture, a ring (24) formed at the distal end of the suture is positioned in jaws of said grasping means and said jaws are closed around said ring before introducing the grasping means into the work channel of said sheath and before fixing said at least one clip to the tissue to be excised.

35. A method for endoluminally or laparoscopically excising a tissue sample from areas in a patient's body according to claim 31, in which the step of introducing said at least one clip into the patient's body and of fixing said clip to the tissue to be excised is carried out under the visual control of a visualization device.

36. A method for endoluminally or laparoscopically excising a tissue sample from areas in a patient's body according to claim 35, in which the step of introducing said traction means into the patient's body comprises the step of inserting said grasping means through said visualization device outside of the patient's body, and then of introducing said visualization device and said grasping means into the work channel of said sheath to fix said traction means to the tissue to be excised.

37. A method for endoluminally or laparoscopically excising a tissue sample from areas in a patient's body according to claim 36, in which said suture is slotted into a channel of said visualization device before introducing said visualization device and said grasping means into the work channel of the sheath, the proximal end of the suture extending outside of said visualization device and of the patient's body.

38. A method for endoluminally or laparoscopically excising a tissue sample from areas in a patient's body according to claim 36, also comprising the step of withdrawing said grasping means and said visualization device from the work channel of the sheath after having fixed said traction means to the tissue to be excised.

39. A method for endoluminally or laparoscopically excising a tissue sample from areas in a patient's body according to claim 31, in which the step of introducing said surgical stapling device into the patient's body is carried out by inserting said surgical stapling device through the sheath, inside the work channel, from the proximal end to the distal end of the sheath, the proximal end of the suture being inserted into the window of the surgical stapling device.

40. A method for endoluminally or laparoscopically excising a tissue sample from areas in a patient's body according to claim 39, in which the suture is re-inserted into the visualization device from outside of the patient's body and the visualization device follows the surgical stapling device and is arranged in a concavity of the surgical stapling device during introduction into the sheath.

41. A method for endoluminally or laparoscopically excising a tissue sample from areas in a patient's body according to claim 25, in which the step of introducing said surgical stapling device into the patient's body is carried out by inserting said surgical stapling device through said sheath, inside of the work channel, from the proximal end to the distal end of the sheath, before pulling the tissue to be excised through said window of the surgical stapling device and before cutting the tissue pulled through said window.

42. A method for endoluminally or laparoscopically excising a tissue sample from areas in a patient's body according to claim 41, in which the step of introducing said surgical stapling device into the patient's body is carried out by guiding said surgical stapling device inside the work channel of the sheath.

43. A method for endoluminally or laparoscopically excising a tissue sample from areas in a patient's body according to claim 42, in which said surgical stapling device is guided inside the work channel sliding along a rail of the sheath.

44. A method for endoluminally or laparoscopically excising a tissue sample from areas in a patient's body according to claim 41, in which said proximal portion of said traction means is inserted into the window of said surgical stapling device, outside of the patient's body, before introducing said surgical stapling device into said sheath.

45. A method for endoluminally or laparoscopically excising a tissue sample from areas in a patient's body according to claim 44, in which said surgical stapling device is guided by said traction means whilst the surgical stapling device is introduced into said sheath.

* * * * *